United States Patent [19]

DeSalle et al.

US005786144A

[11] Patent Number: 5,786,144
[45] Date of Patent: Jul. 28, 1998

[54] METHOD AND COMPOSITIONS FOR IDENTIFICATION OF SPECIES ORIGIN OF CAVIAR

[75] Inventors: Rob DeSalle; Vadim J. Birstein, both of New York, N.Y.

[73] Assignee: American Museum of Natural History, New York, N.Y.

[21] Appl. No.: 647,584

[22] Filed: May 13, 1996

[51] Int. Cl.$^6$ .............................. C12Q 1/68; C12P 19/34; C07H 21/02; C07H 21/04
[52] U.S. Cl. ........................ 435/6; 435/91.2; 536/23.1; 536/24.3; 536/24.33
[58] Field of Search ................. 435/6, 91.2; 536/23.1, 536/24.3, 24.33

[56] References Cited

U.S. PATENT DOCUMENTS

4,683,195  7/1987  Mullis et al.
4,683,202  7/1987  Mullis.

FOREIGN PATENT DOCUMENTS

9205277  4/1992  WIPO.

OTHER PUBLICATIONS

Birstein, et al. Tetraploid–Octoploid relationships and karyological evolution in the order Acipenseriformes (Pisces) Karyotypes, nucleoli, and nucleolus–organizer regions in four aceipenserid species, Genetica.vol. 73, pp. 3–12 (1987).

Walsh, et al., "Chelex 100 as a Medium for Simple Extraction of DNA for PCR-Based Typing from Forensic Material", Biotechniques, vol. 10, No. 4, pp. 506–513 (1991).

Keyvanfan, A.C. et al C.R. Acad Sc. Paris Ser III No. 9, vol. 304, pp. 191–193, 1987.

Baker et al., "Which whales are hunted? A molecular genetic approach to monitoring whaling", American Assoc. for the Advancement of Science, Science, vol. 265, pp. 1538–1539.

Birstein, V.J., "Sturgeons and Paddlefishes: Threatened Fishes in Need of Conversation", Conserv. Biol., vol. 7, pp. 773–787 (1993).

Brown, J.R., et al., "Nucleotide Sequence of the apocytochrome B Gene in White Surgeon Mitochondrial DNA", Nucleic Acids Research, vol. 17 (11), p. 4389 (1989).

Brown, J.R., et al., "Length Variation, Heteroplasmy and Sequence Divergence in the Mitocondrial DNA of Four Species of Sturgeon (*Acipenser*)", Genetics, vol. 142, pp. 525–535 (1996).

Cronin, et al., Wildlife Society Bulletin, vol. 19, pp. 94–105 (1991).

DeSalle, R. et al., "Molecular Evolution: Producing the Biochemical Data", Methods in Enzymology, vol. 224, pp. 176–204 (1993).

Gardiner, B.G., "Sturgeons as Living Fossils", Living Fossils, eds. Eldredge, N. & Stanley, S.M., Living Fossils, pp. 148–152 (1984).

Graves, et al., "Biochemical Genetics of Southern California Basses of the Genus Paralabrax: Specific Identification of Fresh and Ethanol–preserved individual Eggs and Early Larvae", Fishery Bulletin, vol. 88, pp. 59–66 (1989).

Hedges, et al., "Caecilian Phylogeny and Biogeography Inferred from Mitochondrial DNA Sequences of the 12S rRNA and 16S rRNa Genes (Amphibia: Gymnophion A)", Herpetological.

Kocher, et al., "Dynamics of mitochondrial DNA evolution in animals: Amplificatin and sequencing with conserved primers", Proceedings of the Natl. Academy of Science of the USA, vol. 86, pp. 6169–6200 (1989).

Meyer, et al., "Origin of Tetrapods Inferred from Their Mitochondrial DNA Affiliation to Lungfish", J. Mol. Evol., vol. 31, pp. 359–364 (1990).

Milner–Gulland and Mace, "The Implact of the Ivory Trade on the African Elephant Loxodonta africana Population as Assessed by Data from the Trade", Biological Conservation, vol. 55.

Miracle, A.L. & Campton, D.E., "Tandem Repeat Sequence Variation and Length Heteroplasmy in the Mitochondrial DNA D–Loop of the Threatened Gulf of Mexico Sturgeon, *Acipenser oxyrhynchus desotoi*", Journal of Heredity, vol. 86(1), pp. 22–27 (1995).

Ong, T.L., et al., "Genetic Divergence between *Acipenser oxyrinchus oxyrichus* and *A. o. desotoi* as Assessed by Mitochondrial DNA Sequencing Analysis", COPEIA 2, (1996).

Rehbein, H.Z., "Caviare: Proximate Composition, Amino Acid Content and Identification of Fish Species", LEBENSM. Unters. Forsch. vol. 180, pp. 457–462 (1985).

Amato et al., "PCR assays of variable nucleotide sites for identification of conservation units," in Molecular Approaches to Ecology and Evolution, Schierwater, B. et al., eds.

Birstein, et al., Genetica, vol. 73, pp. 3–12 (1993).

Palumbi, et al., The Simple Fool's Guide to PCR, Biol. 101, Version 2 (1991).

Walsh, et al., Bio. Techniques, vol. 10, pp. 506–513 (1991).

Keyvanfar A. Am Inst. Oceanog? (Paris) vol. 64 pp. 25–64, 1988 for considered Feb. 16, 1998.

Brown et al. Genetics 142: 525–535, 1996.

DeSalle et al. Methods in Enzymology 224: 176–204, 1993.

Hara et al. Bulletin of the Japan Sea NAtional Fisheries Research Institute (Abstract provided) vol. 44: 131–138, 1994.

*Primary Examiner*—W. Gary Jones
*Assistant Examiner*—Dianne Rees
*Attorney, Agent, or Firm*—Weil, Gotschal & Manges; Peter Tu; Kevin McMahon

[57] ABSTRACT

The present invention provides a method and compositions for species identification from small samples of fish tissue. The method includes the use of the polymerase chain reaction (PCR) to amplify regions of the mitochondrial genome from total cellular DNA with species-specific primers and subsequent analysis of the PCR products. The method provides an accurate and rapid determination of the species of origin for a single egg of processed caviar. Compositions for PCR primers specific for 27 species of sturgeon are provided.

13 Claims, 4 Drawing Sheets

* TM is the theoretical melting temperature of the primer. Ovals indicate final decisions on annealing temperatures. Rectangles indicate stages where further tests are needed.

5,786,144

SEQUENCE LISTING ( 1 ) GENERAL INFORMATION:

( i i i ) NUMBER OF SEQUENCES: 145

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATTAAAGTTG TTGCGGTTT                                                                   1 9

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGTGGCATTT TATTTTATTA GAGG                                                2 4

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CCGGTCTGAA CTCAGATCAC GT                                                2 2

( 2 ) INFORMATION FOR SEQ ID NO:4:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

CGCCTGTTTA CCAAAACAT 19

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CCGGTCTGAA TCAGATCACG T 21

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AAACTGCAGC CCCTCAGAAT GATATTTGTC CTCA 34

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CGAAGCTTGA TATGAAAAAC CATCGTTG 28

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GCAAACGGGG CCTCCTC 17

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CAGAATGATA TTTGGCCTCA  20

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CACTACACAG CTGACATC  18

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CAGAATGATA TTTGGCCTCA  20

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CTTTCTGCCT TCCCGTAT  18

( 2 ) INFORMATION FOR SEQ ID NO:13:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GAAGAAAGTG GAAGGCG  17

( 2 ) INFORMATION FOR SEQ ID NO:14:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
GGAGTCCTAG GCCCTCCTG                                                                       19
```

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CCTCCAATTC ATGTGAGTAC T                                                                    21
```

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
AATAAACTAG GTGGAGTT                                                                        18
```

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
CCTCCAATTC ATGTGAGTAC T                                                                    21
```

( 2 ) INFORMATION FOR SEQ ID NO:18:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
ATGAATCTGA GGCGGCTTC                                                                       19
```

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

```
GAAGAAAGTG GAAGGCG                                                                         17
```

( 2 ) INFORMATION FOR SEQ ID NO:20:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

CGCAACCGTG ATCACCAACC TCCTTTA    27

( 2 ) INFORMATION FOR SEQ ID NO:21:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:21:

CGCAACCGTG ATCACCAACC TCCTTTCT    28

( 2 ) INFORMATION FOR SEQ ID NO:22:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:22:

CGCAACCGTG ATCACTAACC TCCTTTCCGC T    31

( 2 ) INFORMATION FOR SEQ ID NO:23:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:23:

CCTCCTTTCC GCCTTCCCCT ACATCGGG    28

( 2 ) INFORMATION FOR SEQ ID NO:24:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:24:

CCTCCTTTCC GCCTTCCCCT AGATCGGA    28

( 2 ) INFORMATION FOR SEQ ID NO:25:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:25:

TCTCCGCCTT CCCATACATC GGCGACACG    29

( 2 ) INFORMATION FOR SEQ ID NO:26:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

TCTCCGCCTT CCCCTACATC GGGGACACC    29

( 2 ) INFORMATION FOR SEQ ID NO:27:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

TTCCCATACA TCGGCGACAC GCTAGG    26

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

TTCCCATACA TCGGCGACAC GCTAGGTCAG    30

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TCTCCGCCTT CCCGTACATC GGCGACACAT    30

( 2 ) INFORMATION FOR SEQ ID NO:30:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

GACACCCTAG TACAATGAAT CTGAGGT 27

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GACACACTAG TACAATGAAT CTGAGGT 27

(2) INFORMATION FOR SEQ ID NO:32:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

AGTTCAATGA ATCTGAGGCG GCTTTTCAC 29

(2) INFORMATION FOR SEQ ID NO:33:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

TGGGTTCTCA GTAGACAACG CCACCCTA 28

(2) INFORMATION FOR SEQ ID NO:34:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

TGGGTTCTCA GTAGACAACG CCACCCTG 28

(2) INFORMATION FOR SEQ ID NO:35:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

TAGACAATGC CACCCTTACC CGATTCTTT 29

(2) INFORMATION FOR SEQ ID NO:36:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:36:

ACCCTAACCC GATTCTTCGC CTA    23

( 2 ) INFORMATION FOR SEQ ID NO:37:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:37:

CCCGATTTTT CGCCTTCCAC TTTG    24

( 2 ) INFORMATION FOR SEQ ID NO:38:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:38:

ATACATCGGC GACACACTAG TG    22

( 2 ) INFORMATION FOR SEQ ID NO:39:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:39:

TCACTAACCT CCTCTCCGCC TTTCCGTAT    29

( 2 ) INFORMATION FOR SEQ ID NO:40:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:40:

CTTTTCAGTA GACAACGCCA CCCTTAG    27

( 2 ) INFORMATION FOR SEQ ID NO:41:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:41:

TACAATGAAT CTGAGGCGGC TTC    23

( 2 ) INFORMATION FOR SEQ ID NO:42:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

CCGATTCTTC GCCTTCCACT TC    22

( 2 ) INFORMATION FOR SEQ ID NO:43:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

CACCCCACA CATCAAACCC GAATGG    26

( 2 ) INFORMATION FOR SEQ ID NO:44:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

GTGATACTTC CTCTTTGCCT ACGCCATCCT T    31

( 2 ) INFORMATION FOR SEQ ID NO:45:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

TTTGCCTACG CCATTCTCCG ATCCATCCT    29

( 2 ) INFORMATION FOR SEQ ID NO:46:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

CGATCTATCC CAAACAAACT AGGCGGAGTC 30

( 2 ) INFORMATION FOR SEQ ID NO:47:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

ACAAACTAGG TGGGGTACTG GCCCTACTT 29

( 2 ) INFORMATION FOR SEQ ID NO:48:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

ACAAACTAGG CGGAGTCCTA GCCCTCCTG 29

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

GGAGTACTAG CCCTACTATT A 21

( 2 ) INFORMATION FOR SEQ ID NO:50:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

GAGTACTAGC CCTTCTATTT TCCATCCTG 29

( 2 ) INFORMATION FOR SEQ ID NO:51:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

GCCCTTCTAT TTTCCATCCT GGTCCTAG 28

( 2 ) INFORMATION FOR SEQ ID NO:52:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:52:

GCCCTTCTAT TTTCCATCCT GGTCCTAGC      29

( 2 ) INFORMATION FOR SEQ ID NO:53:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:53:

TAGTGCCAAT GCTTCACACC TCTAAG      26

( 2 ) INFORMATION FOR SEQ ID NO:54:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:54:

CAAACAACGA GGAAATACAT TTCGGCCT      28

( 2 ) INFORMATION FOR SEQ ID NO:55:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:55:

GAGGAAATAC ATTTCGGCCT CTCTCCCAAG      30

( 2 ) INFORMATION FOR SEQ ID NO:56:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:56:

CGCCATTCTC GGAAACACAT TCCGACCCCT CCGGT      35

( 2 ) INFORMATION FOR SEQ ID NO:57:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear (i i) MOLECULE TYPE: DNA (genomic)

(x i) SEQUENCE DESCRIPTION: SEQ ID NO:57:

CGCCATTCTC GGAAACACAT TCCGACCCCT CCG  33

(2) INFORMATION FOR SEQ ID NO:58:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:58:

ATTCTCGGAA ACACATTCCG ACCCCTTTCT CAAATG  36

(2) INFORMATION FOR SEQ ID NO:59:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:59:

ATTCTGGACC CTAGTGGCGA CATACTAGTG  30

(2) INFORMATION FOR SEQ ID NO:60:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:60:

CTCAAATCCT ATTCTGGACC TAGTAGGT  28

(2) INFORMATION FOR SEQ ID NO:61:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:61:

ATTATTTCTC GCAATACACT AT  22

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:62:

GCAATACACT ACACAGCTGG 20

(2) INFORMATION FOR SEQ ID NO:63:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

GCAATACACT ACACAGCTGA CATC 24

(2) INFORMATION FOR SEQ ID NO:64:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

CACATCTGCC GAGACGTAAA TTAT 24

(2) INFORMATION FOR SEQ ID NO:65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

GCCCACATCT GCCGGGATGT AAATTACGGC 30

(2) INFORMATION FOR SEQ ID NO:66:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

GCCCACATCT GCCGGGATGT AAATTACGGC TGAT 34

(2) INFORMATION FOR SEQ ID NO:67:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

GCCCACATCT GCCGAGACGT AAATTACGGA TA 32

(2) INFORMATION FOR SEQ ID NO:68:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:68:

AGATGTAAAT TACGGATGGC TT        22

( 2 ) INFORMATION FOR SEQ ID NO:69:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

ACGGGTGACT AATCCGAAAC G        21

( 2 ) INFORMATION FOR SEQ ID NO:70:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

CGAAACGTCC ACGCAAATGG C        21

( 2 ) INFORMATION FOR SEQ ID NO:71:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:71:

CGAGATGTGA ATTACGGATG C        21

( 2 ) INFORMATION FOR SEQ ID NO:72:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

GGATGTAAAT TACGGCTGAT TAATCCGC        28

( 2 ) INFORMATION FOR SEQ ID NO:73:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (ii) MOLECULE TYPE: DNA (genomic)

(xi) SEQUENCE DESCRIPTION: SEQ ID NO:73:

CCTCCGTCGC CCACATCTGT 20

(2) INFORMATION FOR SEQ ID NO:74:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:74:

AAATATTCAT GCAAACGGGG CT 22

(2) INFORMATION FOR SEQ ID NO:75:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:75:

TCCGAAATAT TCATGCAACG GGGCCTCCTC 30

(2) INFORMATION FOR SEQ ID NO:76:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:76:

ATCTTCACGT AGCACGAGGT T 21

(2) INFORMATION FOR SEQ ID NO:77:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:77:

ATCTTCACGT AGCACGAGGT TTGTAT 26

(2) INFORMATION FOR SEQ ID NO:78:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:78:

CGGGGTATAT ACTATGGTTC G                                                         2 1

( 2 ) INFORMATION FOR SEQ ID NO:79:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:79:

TCCAAAAAGA AACCTGAAAT                                                           2 0

( 2 ) INFORMATION FOR SEQ ID NO:80:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

CGTAGCACGA GGTTTGTATT ACGGTTCATA CCTT                                           3 4

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:81:

GCATGTACTA CGCTTCCTAT                                                           2 0

( 2 ) INFORMATION FOR SEQ ID NO:82:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:82:

GTTCATACCT CCAAAAAGAG                                                           2 0

( 2 ) INFORMATION FOR SEQ ID NO:83:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:83:

GTGTCGCCGA TGTACGGGAA GGCGT                                                     2 5

( 2 ) INFORMATION FOR SEQ ID NO:84:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:84:

GTGTCGCCGA TATACGGGAA GGCA 24

( 2 ) INFORMATION FOR SEQ ID NO:85:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:85:

GTGTCGCCGA TGTACGGGAA A 21

( 2 ) INFORMATION FOR SEQ ID NO:86:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:86:

CTCAGATTCA TTGTACTAGG GTGTCC 26

( 2 ) INFORMATION FOR SEQ ID NO:87:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:87:

CTCAGATTCA TTGTACTAGT GTGTCT 26

( 2 ) INFORMATION FOR SEQ ID NO:88:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:88:

CTCAGATTCA CTGACCTAGC 20

( 2 ) INFORMATION FOR SEQ ID NO:89:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear (i i) MOLECULE TYPE: DNA (genomic)

(x i) SEQUENCE DESCRIPTION: SEQ ID NO:89:

CTCAGATTCA TTGTACTAGG    20

(2) INFORMATION FOR SEQ ID NO:90:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:90:

GTTGTCCACT GAAAAGCCGC CTCAGATTCA CTGAC    35

(2) INFORMATION FOR SEQ ID NO:91:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:91:

GTTGTCCACT GAAAAGCCGC CTCAGATTCA C    31

(2) INFORMATION FOR SEQ ID NO:92:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:92:

GAAAAGCCGC CTCAGATTCA TTGCACTAA    29

(2) INFORMATION FOR SEQ ID NO:93:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:93:

TTAGGGTGGC GTTGTCTACT GAGAACCCA    29

(2) INFORMATION FOR SEQ ID NO:94:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:94:

GGGTGGCGTT GTCTACTGAA AAGCCA                                                    26

( 2 ) INFORMATION FOR SEQ ID NO:95:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:95:

GGGTAAGGGT GGCATTGTCT AG                                                        22

( 2 ) INFORMATION FOR SEQ ID NO:96:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:96:

GTGGTAGGCG AAGAATCGGG TT                                                        22

( 2 ) INFORMATION FOR SEQ ID NO:97:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:97:

GTGGAAGGCG AAGAATCGGG TC                                                        22

( 2 ) INFORMATION FOR SEQ ID NO:98:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:98:

GGTAGGAGAA AGTGGAAGGC A                                                         21

( 2 ) INFORMATION FOR SEQ ID NO:99:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:99:

CTTACGGTAG AAGAAAGTGG T                                                         21

( 2 ) INFORMATION FOR SEQ ID NO:100:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:100:

GCTAGCTCCG GCGATTACGA ATGGTAGAAC  30

( 2 ) INFORMATION FOR SEQ ID NO:101:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:101:

AGCCGCCTCA GATTCATTGC  20

( 2 ) INFORMATION FOR SEQ ID NO:102:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:102:

GTACTAGTGT GTCGCCGATA  20

( 2 ) INFORMATION FOR SEQ ID NO:103:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:103:

AGTGGAAGGC GAAAAATCGG C  21

( 2 ) INFORMATION FOR SEQ ID NO:104:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:104:

AGGGTGGCGT TGTCTACTGA G  21

( 2 ) INFORMATION FOR SEQ ID NO:105:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:105:

AGCTCCGGCG ATTACAAATG GCAGGAGG  28

( 2 ) INFORMATION FOR SEQ ID NO:106:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:106:

GAGAATGGCG TAGGCAAAGA GAAAGTAC  28

( 2 ) INFORMATION FOR SEQ ID NO:107:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:107:

AGTTTGTTTG GGATGGATCG A  21

( 2 ) INFORMATION FOR SEQ ID NO:108:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:108:

TACTCCACCT AGTTTATTTA  20

( 2 ) INFORMATION FOR SEQ ID NO:109:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:109:

ATAGAGAACA GGAGGGCTAG G  21

( 2 ) INFORMATION FOR SEQ ID NO:110:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:110:

ATTAGTACTA GGATGGAGAA A                                                                                      21

( 2 ) INFORMATION FOR SEQ ID NO:111:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:111:

ATTAGTACTA GGATAGAGAA C                                                                                      21

( 2 ) INFORMATION FOR SEQ ID NO:112:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:112:

AGTATTAGTA CTAGGATGGA T                                                                                      21

( 2 ) INFORMATION FOR SEQ ID NO:113:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:113:

TTGGTACCAA TGCTAGGACC                                                                                        20

( 2 ) INFORMATION FOR SEQ ID NO:114:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:114:

TGGAGTATTG GTACCAATGC                                                                                        20

( 2 ) INFORMATION FOR SEQ ID NO:115:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:115:

TGGAGTATTG GTACCAATG                                                                                         19

( 2 ) INFORMATION FOR SEQ ID NO:116:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:116:

CGAAACGTGT TTCCTCGTTG                    20

( 2 ) INFORMATION FOR SEQ ID NO:117:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:117:

AAAATAGGAC TTGGGAGAGA                    20

( 2 ) INFORMATION FOR SEQ ID NO:118:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:118:

CCACTAGGGC TCAAAATAGG AC                 22

( 2 ) INFORMATION FOR SEQ ID NO:119:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:119:

AGGGCCCAGA ATAGGATTTA                    20

( 2 ) INFORMATION FOR SEQ ID NO:120:

( i ) SEQUENCE CHARACTERISTICS:
   ( A ) LENGTH: 22 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:120:

AGGGCCCAGA ATAGGATTTA CC                 22

( 2 ) INFORMATION FOR SEQ ID NO:121:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:121:

GCCACTAGGG CCCAGAATAG C    21

( 2 ) INFORMATION FOR SEQ ID NO:122:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:122:

GGGTGTTCGA CTGGTTGGCC TCCGATTCAT GTGAGC    36

( 2 ) INFORMATION FOR SEQ ID NO:123:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:123:

ATGTGAGTAC TAACATATCA    20

( 2 ) INFORMATION FOR SEQ ID NO:124:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:124:

CTGTTGAAAT GTCAGCTGTA    20

( 2 ) INFORMATION FOR SEQ ID NO:125:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:125:

GGAGAAGGCT GTTGAAATGC    20

( 2 ) INFORMATION FOR SEQ ID NO:126:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:126:

CGGAGGAGAA GGCTGTTGAG 20

( 2 ) INFORMATION FOR SEQ ID NO:127:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:127:

ATATTTCGGA TTAGTCATCC A 21

( 2 ) INFORMATION FOR SEQ ID NO:128:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:128:

GCATGAATAT TGCGGATTAA TCAG 24

( 2 ) INFORMATION FOR SEQ ID NO:129:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:129:

GCATGAATAT TGCGGATTAA 20

( 2 ) INFORMATION FOR SEQ ID NO:130:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:130:

CATGAATATT TCGGATTAGT T 21

( 2 ) INFORMATION FOR SEQ ID NO:131:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:131:

TTTGCATGAA TATTTCGGAT A 21

( 2 ) INFORMATION FOR SEQ ID NO:132:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:132:

AGGAGGCGCC ATTTGCGTGG AC          22

( 2 ) INFORMATION FOR SEQ ID NO:133:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:133:

CAGATAAAGA AGAAGGAGGC G           21

( 2 ) INFORMATION FOR SEQ ID NO:134:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:134:

GCATGAATGT TTCGGATTAG G           21

( 2 ) INFORMATION FOR SEQ ID NO:135:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:135:

ATGAATATTG CGGATTAATC AG          22

( 2 ) INFORMATION FOR SEQ ID NO:136:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:136:

CATCCGTAGT TAACATCTCG A           21

( 2 ) INFORMATION FOR SEQ ID NO:137:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:137:

AGCAGATAAA GAAGAAAGAA                                                                     20

( 2 ) INFORMATION FOR SEQ ID NO:138:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:138:

TTTTGAAGGT ATGAACCGTA ATACAA                                                              26

( 2 ) INFORMATION FOR SEQ ID NO:139:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:139:

TTTTGAAGGT ATGAACCGTA A                                                                   21

( 2 ) INFORMATION FOR SEQ ID NO:140:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:140:

CGTGAAGATA CAAGCAGATG AAGAAGG                                                             27

( 2 ) INFORMATION FOR SEQ ID NO:141:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:141:

CAGGTTTCTT TTTGGAGGTA C                                                                   21

( 2 ) INFORMATION FOR SEQ ID NO:142:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:142:

```
GGTGAGAAGC AAGAGGAATA CTCCAATA                                                                    2 8
```

( 2 ) INFORMATION FOR SEQ ID NO:143:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:143:

```
ATGTTTCAGG TTTCTTTTTG A                                                                           2 1
```

( 2 ) INFORMATION FOR SEQ ID NO:144:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:144:

```
TTTCAGGTTT CTTTTGGAG A                                                                            2 1
```

( 2 ) INFORMATION FOR SEQ ID NO:145:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:145:

```
ATACTCCGAT GTTTCAGGTC                                                                             2 0
```

METHOD AND COMPOSITIONS FOR IDENTIFICATION OF SPECIES ORIGIN OF CAVIAR

INTRODUCTION

TECHNICAL FIELD

The present invention is related to the identification of the species origin of fish eggs and involves the use of the polymerase chain reaction (PCR) to amplify regions of the mitochondrial genome from total cellular DNA with species-specific primers and subsequent analysis of the PCR products.

BACKGROUND

Species identification using genetic markers has become an important part of conservation studies in vertebrates. The order Acipenseriformes is an ancient group of fishes ("living fossils"), which includes sturgeons from the family Acipenseridae and paddlefishes from the family Polyodontidae (Gardiner, B. G. in *Living Fossils*, eds., Eldredge, N. & Stanley, S. M., Springer Verlag, New York, 1984, pp. 148–152). Almost all of the 27 members of the order Acipenseriformes are now endangered [Birstein, V. J. *Conserv. Biol.* 7, 773–787 (1993)]. Sturgeons are primarily known as producers of caviar and uncontrolled overfishing threatens the survival of many species. The three commercial Russian species inhabiting the Volga River-Caspian Sea basin, the beluga sturgeon, *Huso huso*, the Russian sturgeon, *Acipenser gueldenstaedti*, and the servuga sturgeon, *A. stellatus*, are especially vulnerable because of the great value of their eggs. The beluga sturgeon is the source of beluga caviar, the most highly prized, while the Russian sturgeon yields osetra and the servuga sturgeon, servuga caviar. Identification of sturgeon species is essential for monitoring the use of these fish in the caviar industry as worldwide populations become smaller and smaller.

In the absence of a reliable method of species identification, caviar dealers have relied upon the appearance, smell, texture and color of the roe and the size of eggs in a crude attempt to identify a particular shipment of caviar by species. Isoelectric focusing of egg soluble proteins on ultrathin polyacrylamide gels has been used for caviar species identification [Rehbein, H. Z. *Lebensm. Unters. Forsch.* 180, 457–462 (1985)]. This approach suffers from the fact that large amounts (2–20 g or roughly 100 and more eggs) of material are needed for the assay. Also, this method can be unreliable [Keyvanfar, A. C., et al., *R. Acad. Sci. Paris* 304, Ser. III, 191–193 (1987); Keyvanfar, A. *Ann. Inst. Oceanogr. (Paris)* 64, 25–64 (1988)].

An international demand for high quality caviar encourages poaching in regulated, but overfished commercial sturgeon populations. Fragile, traditionally non-commercial species are being increasingly substituted for the disappearing commercial species. A reliable, inexpensive species identification test for monitoring the production and importation of caviar is important for purposes of enforcing conservation strategies throughout the world.

The large number of eggs required for a protein electrophoresis identification test is a further problem because commercial caviar can be a mixture of the roe from two or more sturgeon species. Such mixtures will yield electrophoresis patterns that will be the sum of the electrophoresis patterns of the mixed species. These mixed patterns are uninterpretable unless the component parts of the sum can be separately identified. Because a large quantity of eggs is required for the protein electrophoresis method, separation and identification of the component parts is impractical. Therefore, a reliable method for caviar species identification from single eggs is needed.

Relevant Literature

Full and partial sequences for various mitochrondrial genes for certain sturgeon species are known: J. R. Brown et al., *Nucl. Acids Res.* 17(11) 4389 (1989); J. R. Brown et al., *Genetics* 142, 525–535 (1996); T.-L. Ong et al., *Copeia* 2,464,469 (1996); and A. L. Miracle and D. E. Campton *J. Heredity* 86(1), 22–27 (1995).

Amato and Gatesy used PCR assays involving mtDNA species-specific haplotypes in crocodiles and caiman to identify the species source of skins used in the production of leather items ["PCR assays of variable nucleotide sites for identification of conservation units," in *Molecular Approaches to Ecology and Evolution*, Schierwater, B. et al., eds., 215–226 (1993)]. Baker and Palumbi identified the species origin of processed whale meat using a portable laboratory equipped to perform the polymerase chain reaction [Science 265, 1538–1539 (1994)]. Cronin, et al., [*Wildl. Soc. Bull.* 19: 94–105 (1991)] and Milner-Gulland and Mace [*Biol. Conservation* 55: 215–229 (1991)] have also used genetic markers in conservation studies.

Graves et al. used restriction fragment length polymorphism techniques on mtDNA obtained from various Paralabrax (bass) tissues including a single mature egg to identify different species [*Fish. Bull.* 88. 59–66 (1989)]. Davidson and Bartlett, PCT application WO 92/05277, disclose a PCR-based method for determining the genus species origin of processed food products and PCR primer compositions comprised of coding sequences of cyt b genes of tuna fish species.

SUMMARY OF THE INVENTION

The present invention provides a method and compositions for species identification from small samples of fish tissue. The method includes the use of the polymerase chain reaction (PCR) to amplify regions of the mitochondrial genome from total cellular DNA with species-specific primers and subsequent analysis of the PCR products. The method provides an accurate and rapid determination of the species of origin for a single egg of processed caviar. Compositions for PCR primers specific for 27 species of sturgeon are provided.

The method includes the steps of: removing salt and other debris from the outer surface of a sample of caviar; isolating clean template DNA; running PCR on the clean template DNA using a cocktail of primers containing at least a pair of primers in which one primer is specific for a sturgeon species of interest and the other primer is a matched anchor; assaying the PCR reaction products and detecting the results. Optionally, the steps of the method may be repeated using primers specific for different species until a positive identification is made. An embodiment of the invention relates to the composition of primers specific for servuga, osetra and beluga caviar species of origin and the composition of additional primers specific for the other twenty-four known, living species of sturgeon.

DETAILED DESCRIPTION OF THE SPECIFIC EMBODIMENTS

Figure 1:
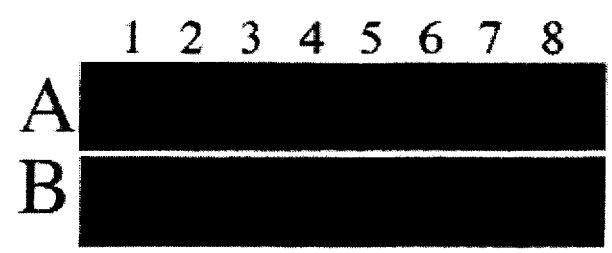
FIG. 1 shows the results of PCR assays run on DNA from single caviar eggs prepared using different procedures. Panel A shows PCR products obtained from template DNA purified by boiling a single, crushed egg with 5% Chelex. Panel B shows PCR products obtained from template DNA purified by phenol/chloroform extraction. In both Panels, Lane 1 shows the results obtained when an egg was processed without washing; Lane 2 shows results from eggs prewashed with 0.525% sodium hypochlorite before crushing; Lane 3 shows eggs pre-washed in homogenization buffer; Lane 4 shows DNA preparation blanks; and Lane 5 shows negative PCR controls. Only Lanes B2 and B3 show PCR products. Panel A, Lanes 6, 7 and 8 show PCR products produced from template DNA purified by the Chelex method from other sturgeon tissue; Lane 6 is the Chelex preparation blank, Lane 7 is a Chelex preparation from *A. stellatus* blood used as a positive control, and Lane 8 is a negative PCR control. Lanes 6, 7 and 8 in Panel B are deliberately left blank.

As used herein, the term "caviar" refers to edible fish eggs, processed by a number of methods known to those skilled in the art. In the case of commercially available food product, caviar is prepared from immature eggs still confined in the fish ovary in a hard, solid formation (hard roe). Alternatively, caviar includes mature fish eggs, fresh, processed or preserved in alcohol and the like. Caviar prepared as food product includes immature or mature eggs obtained from carp, herring, pollock, bleak, lumpfish, pink salmon, whitefish, chum salmon, trout, flying fish, and bowfish. Preferably, the source of the fish eggs is sturgeon or salmon roe, with sturgeon eggs being most preferable.

The term "primer," as used herein, refers to a single stranded DNA oligonucleotide sequence, preferably produced synthetically, which is capable of acting as a point of initiation for synthesis of a primer extension product that is complementary to a nucleic acid strand to be copied. In the case of primers intended for use in synthesizing mitochondrial DNA molecules by PCR products, the length of the primer must be sufficient to prime the synthesis of extension products in the presence of a polymerization enzyme. Preferably, the length of the primer is from about 10 to 50 nucleotides, more preferably from about 15 to 25, and most preferably from about 17 to 21 nucleotides. Primers of the invention are of sufficient length that random priming does not occur; that is, the primers anneal only to unique and diagnostic segments of the genome. Longer primers may be used in the invention, although primers of no more than about 50 nucleotides are preferred when it is desirable to keep costs low.

The present invention is directed to a PCR-based process for determining the species source for a sample of caviar as small as one egg and is particularly well-suited to identify the three major sources of commercial caviar, osetra, servuga and beluga. Specifically, the method distinguishes osetra caviar, also known as oscetra and ossetra, which are processed immature eggs of the species *A. gueldenstaedti*, from beluga caviar (*H. huso*), from servuga caviar (*A. stellatus*), and from the eggs of all other known living species of sturgeon. Using the method of the present invention, the species origin of a single egg from a sample of commercial caviar can conveniently and inexpensively be determined in about 8 hours or less. A previously known method of Graves et al., for species identification by restriction fragment length polymorphism analysis of mtDNA obtained from single fresh or ethanol-preserved bass fish eggs requires several days to a week for processing as well as considerably more expensive materials.

The method of the present invention is based on the species specificity of the nucleotide sequences of mitochondrial genes. This specificity has been established through examination of sequenced parts of genes for 12S rRNA, 16S rRNA, and cytochrome b (cyt b) mitochondrial genes for all known living sturgeon species. Cyt b gene sequences are the most variable among sturgeon species and were used in the design of the sturgeon-species-specific primer systems. Ordinarily, primers for PCR amplification of DNA are designed to be specific to a constant region of a gene; that is, a region that is conserved across species. Primers specific to a variable region of any gene are useful only for amplification of DNA from the single species from which the gene was obtained, an object of the present invention.

The cyt b gene is well-suited as a primer template for the invention. It codes for a transmembrane protein, the imbedded portions of which are highly conserved across species. The protein makes seven loops through the membrane, all of which are conserved, whereas the regions of protein between the loops are variant. The primers of the present invention are made to the DNA coding for the variant regions of the protein. In a similar fashion, primers made to the DNA coding for variable regions of other proteins may be employed in the process of the present invention.

A key feature of a primer of the invention is that it includes a diagnostic nucleotide position found within the variable region of several individuals known to belong to the species of interest. An appropriate primer must give uniform results with all individuals of a species for that primer to be considered diagnostic for the species. In the case where only a small number of individuals for a species of interest is available, it is desirable to use multiple primers to identify the species to allow for individual variation.

Generally, the method of the present invention involves: preparing a sample of caviar by washing with an agent capable of removing salt and other debris from its outer surface; isolating clean template DNA from the sample; running PCR on the clean template DNA using a cocktail of sturgeon primers containing at least a pair of primers in which one member of the pair is a primer is specific for a sturgeon species of interest and the second member is a matched anchor primer; assaying the PCR reaction products and detecting the results. Optionally, the steps of the method may be repeated using primers specific for different species until a positive identification is made.

Removal of salt and other debris from the outer surface of commercially prepared caviar eggs prior to extraction of template DNA is an important aspect of the invention. This removal may be accomplished by washing with dilute saline solution, buffers such as DNA extraction buffer and the like, dilute aqueous acids or bases, and mild soap and detergent solutions such as sodium dodecyl sulfate (SDS) and the like. The concentration of an active ingredient in the washing solution is such that the solution removes salts and debris, but does not damage the integrity of the eggs being cleaned. Washing with DNA extraction buffer is preferred and washing with a 5–15% vol./vol. dilution of a standard 5.25% solution of sodium hypochlorite, such as commercial Clorox™, is most preferred. By "washing" is meant that the egg or eggs being prepared are contacted with the cleaning solution and the liquid is allowed to run off, thus carrying away salts and any cellular or other debris. Conveniently, about a milliliter of cleaning solution is added to a suitable container holding a single caviar egg, and the egg and solution are gently drawn up and down in a pipette for about three minutes. After the wash period, the solution is gently drawn off from the egg with a pipette such that the caviar is not punctured or otherwise disrupted.

Isolation of clean template DNA from the washed egg or eggs is the next step of the invention. "Quick" DNA preparations that exist for the isolation of DNA from tissues for PCR experiments such as direct amplification (i.e., amplification of the eggs without actual DNA isolation) or Chelex preparations yield DNA of insufficient purity for use in the method of the present invention. Methods yielding highly purified DNA, such as ultracentrifugation in cesium chloride gradients and use of commercial preparation kits such as Sephadex spin columns and GeneClean (BIO 101) glass milk techniques and the like, may be used. Suitable, highly purified DNA is free from enzymes, such as DNAses and RNases, and other proteins that may interfere with the activity of TAQ polymerase used in PCR amplification. Preferably, a phenol/chloroform extraction technique, such as that described by DeSalle, R., et al. [*Methods in Enzymology*. Vol. 224. *Molecular Evolution: Producing the Biochemical Data* (eds. Zimmer, E. A., et al.) 176–204 (Acad. Press, San Diego, 1993)], is used. Briefly, a washed, then crushed, egg is treated with Proteinase K in a buffer at 60° C. for one hour, followed by extraction by centrifugation with aqueous phenol, then chloroform, then ethanol, yielding pelleted DNA. Such a preparation gives large amounts of clean template DNA (0.5 to 1.0 micrograms total DNA per egg) suitable for PCR reactions.

Running PCR using a cocktail of sturgeon primers containing at least a pair of primers in which one primer is specific for a species of interest to amplify the clean template DNA is a further step of the present invention. Amplification of DNA using the polymerase chain reaction is known to those skilled in the art and is generally described in U.S. Pat. Nos. 4,683,195 and 4,683,202 to Mullis. In general, the PCR consists of many repetitions of a cycle that consists of: (a) a denaturation step, which melts both strands of a DNA molecule; (b) an annealing step, which allows added primers to anneal specifically to the melted strands of the DNA molecule; and (c) an extension step, which incorporates to the primers deoxyribonucleotides complementary to those of the strand of DNA to which the primers are annealed. The PCR process may be conducted using a thermocycler apparatus, such as a Cetus Perkin-Elmer 486 Thermal Cycler and a 9600 Thermal Cycler.

Figure 4:
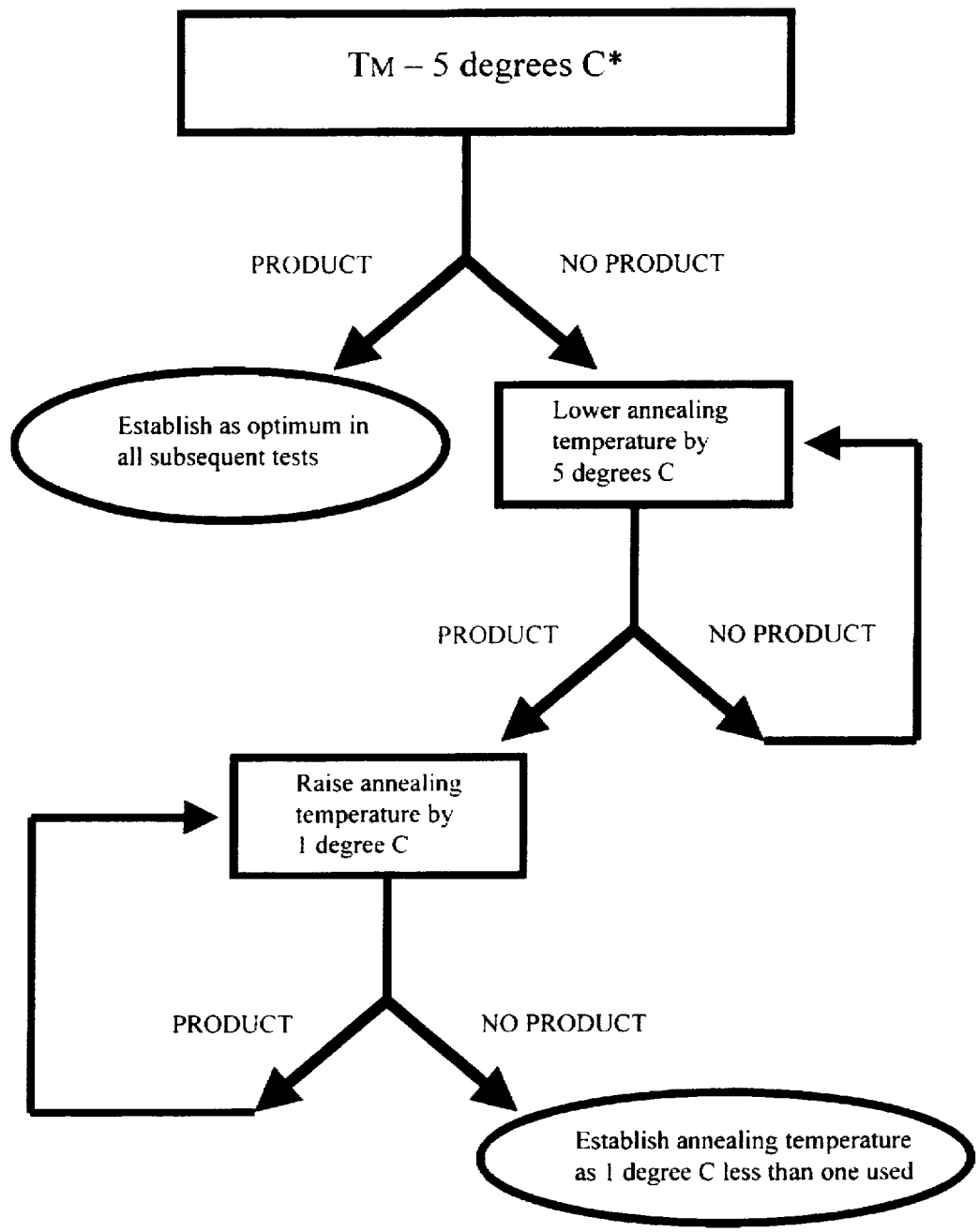
FIG. 4 shows a flow chart for optimization of the PCR procedure.

The conditions used for the PCR will depend on the specific primers used for a given species of interest. The concentrations of primers and buffers used will be apparent from the Examples that follow. The temperature for annealing primers to the template DNA for each primer is optimized as shown in FIG. 4. Beginning at the theoretical melting temperature ($T_M$) minus 5° C. ($T_M$–5° C.), PCR is carried out. If a product is obtained, then no further optimization is required. If no PCR product is obtained, then the annealing temperature is lowered by 5° C. and the process continued until a product is obtained. To determine that this new temperature is indeed the optimum, the annealing temperature is increased by 1° C. increments until no product is observed. The optimum annealing temperature is then established as 1° C. less than the temperature at which no product was produced. Optimization of the number of reaction cycles is dependant upon the concentration of the template DNA. In the method of the present invention, cycle numbers from about 20 to about 40 may be used, with about 25 to 30 cycles being preferred.

The PCR cycles are carried out with at least a pair of primers, one of which is specific for a species of interest, hereinafter the "diagnostic primer," and the other is an "anchor primer." The present invention includes the composition of diagnostic primers specific for each of the three commercial Russian sturgeon species: *H. huso* (beluga), *A. gueldenstaedti* (osetra), and *A. stellatus* (sevruga). The invention further includes the composition of primers specific for the other twenty-four known, living species of sturgeon. The primers may be employed in the method of the present invention as pairs or as a mixture of primer pairs. Employing the primers in matched pairs with one diagnostic primer and one anchor primer is preferred in the case where the sample to be diagnosed is likely to be from one of the three most common commercial species. In the case where the presence of a less common species is suspected, use of a mixture, or "cocktail," containing pairs of primers for identification of two or more species is preferred. In this embodiment, the method of the present invention may be repeated with fewer and fewer primer pairs until the species is positively identified. Alternatively, a cocktail containing diagnostic and anchor primers of varying lengths, such that the resultant PCR products will not overlap when run out on a gel for visualization, may be employed.

A matched anchor primer is designed downstream to the 3' end of the diagnostic member of the primer pair and for the other strand of the double helix. Since PCR proceeds best with two primers placed relatively close to each other (and on opposite strands), the anchor primer is designed to be specific for a part of the gene no more than about 250 nucleotides away from the diagnostic nucleotide position of the diagnostic primer. The anchor primer sequence may begin one nucleotide away from the diagnostic position in either the 3' or the 5' direction, in the case where a complementary diagnostic primer sequence is used. Preferably, the anchor primer sequence occurs from about 50 to about 200 nucleotides away, and most preferably, from about 100 to about 200 nucleotides away. The anchor primer is designed to work with as wide a range of species as possible. The advantage of designing the anchor primer less than about 250 nucleotides away from the diagnostic nucleotide position of the diagnostic primer is that highly degraded DNA samples, such as might be expected from commercially treated caviar, will be amplifiable with such primers. The primers are designed so that a high stringency PCR reaction with primers for a given species gives a positive reaction (a band of the correct length on an agarose gel) and a primer pair that is not specific for a particular species gives a negative reaction (a lack of the PCR band).

Since DNA is synthesized in a 5' to 3' direction and a primer is necessary for synthesis, PCR primers are usually designed in a 5' to 3' direction. The 3'-most base on the primer is critical, because if it does not match perfectly, synthesis is blocked. Diagnostic and anchor primers of the invention match the diagnosable species in all positions of the primer, especially on the 3'-most nucleotide of the primer. The sequences of primers of the invention are given in the Examples following.

The diagnostic and anchor primers of the present invention may be synthesized using any suitable method known to those skilled in the art, such as phosphotriester and phosphodiester methods and the like. Conveniently, primers are synthesized by automated oligonucleotide synthesizers, such as those manufactured by ABI and OPERON. Primers may also be isolated from a naturally occuring or a genetically engineered biological source using appropriate restriction endonucleases that cut double-stranded DNA at or near a nucleotide sequence of interest.

A further step in the method of the present invention is detection of the PCR products. The reactions may be assayed in a number of ways including separation of the products by gel electrophoresis and detection of the resulting bands. The reaction products are preferably assayed on agarose gel in a suitable buffer, such as 1X Tris borate EDTA (TBE) and 1X Tris EDTA acetate (TEA) and the like. The gels may be stained by a variety of methods including with ethidium bromide, propidium iodide or silver. Alternatively, the PCR product fragments may be radioactively end-labeled and visualized after autoradiography or a southern blot can be performed and the presence of fragments observed after probing with a radioactively labeled probe. Preferably, the gels are stained in ethidium bromide and the PCR products visualized under ultraviolet light. The presence/absence of a PCR product is easily detected by the presence or absence of a fluorescent PCR product band on the agarose gel. Positive PCR control reactions are run to ensure that the caviar DNA is of good enough quality to amplify. Negative PCR reactions are run to ensure that there are no contaminating factors that might obscure the results of the assay. Interpretation of the assay is straightforward: presence of a PCR product indicates a match with the target caviar DNA of the particular primer and absence of a PCR product indicates a mismatch with the target caviar DNA.

The primers of the invention, and, optionally, the materials needed to perform the PCR reaction and analysis, may be provided as a kit. The kit may contain appropriate amounts of primer pairs for various species of interest, suitable containers in which to carry out the steps of the invention, supplies of washing solutions, and the like, such that the method of the invention may be conveniently carried out.

An important advantage of the present invention is the capability of the method to isolate useable template DNA from a single egg of commercially processed caviar. Commercial caviar can be a mixture of two or more species. Only by examining several eggs individually from a batch of caviar can this mixing be detected. PCR performed on DNA isolated from large batches of eggs can give positive signals for primers specific for multiple species, thereby causing possible inaccurate diagnosis of the species origin. The method of the present invention is further advantageous because it allows identification of the species origin of caviar eggs that have been roughly treated or subjected to conditions that cause degradation of the DNA.

The present invention can be differentiated from other PCR-based species identification methods in that it depends upon diagnostic characteristics, the diagnostic nucleotide positions, found in all individuals within a species, but not found in individuals outside the species. Other methods, such as that of Davidson and Bartlett, rely on primers conserved across species, and across genera in some cases. The method is therefore unlike conventional fingerprinting, in which one tries to match a found fingerprint against a collection of known fingerprints. Instead, a diagnostic characteristic identifies an individual as a member of a species, as a fingerprint can be identified as human or non-human.

The invention is illustrated by the following non-limiting examples.

EXAMPLES

Example I

Optimization of Method for Preparation of DNA for PCR from Caviar

The amount of gross sample preparation required for single caviar eggs before DNA extraction was first determined. Eggs were treated by different methods, then their total DNA extracted by a standard phenol/chloroform method [DeSalle, R., et al., in *Methods in Enzymology*. Vol. 224. *Molecular Evolution: Producing the Biochemical Data* (eds. Zimmer, E. A., et al.) 176–204 (Acad. Press, San Diego, 1993)], the DNA used as a template for PCR using 150-base control universal primers (Palumbi et al., *The Simple Fool's Guide* to PCR, Version 2, 1991), the PCR products run on 1X TBE 1.0% agarose gels, and the products visualized using ethidium bromide staining and observation under UV light.

Three extraction procedures for the isolation of DNA from processed caviar were tested. The first was a very simple procedure where a single egg was crushed in 100 microliters of 1X PCR buffer. A dilution series of this preparation was performed to examine the suitability of such extracts as templates for PCR. The second method was the standard Chelex preparation [(Walsh et al., *Bio Techniques* 10, 506–513 (1991)], where a dilution series was also used to examine a range of preparation template concentrations. The third method required treatment of a crushed egg in buffer with Proteinase K at 60° C. for one hour followed by a full phenol/chloroform preparation (DeSalle et al., 1993). The first two simple procedures did not produce suitable templates for PCR while the phenol/chloroform extraction procedure did. More importantly, the phenol preparation procedure produced a large quantity of suitable template in that over 1 µg of total DNA was easily isolated from a single egg.

FIG. 1 shows the results of PCR assays run on DNA from single caviar eggs prepared using different egg-washing and DNA extraction procedures. Panel A shows PCR products obtained from template DNA purified by boiling a single, crushed egg with 5% Chelex DNA. Panel B shows PCR products obtained from template DNA purified by phenol/chloroform extraction. In both Panels, Lane 1 shows the results obtained when an egg was processed without washing; Lane 2 shows results from eggs pre-washed with 0.525% sodium hypochlorite before crushing; Lane 3 shows eggs pre-washed in homogenization buffer; Lane 4 shows DNA preparation blanks; and Lane 5 shows negative PCR controls. Only Lanes B2 and B3 show PCR products, demonstrating that the phenol/chloroform extraction procedure performed on eggs pre-washed with either 0.525% sodium hypochlorite or extraction buffer is satisfactory. The Chelex procedure does produce PCR products when used to purify template DNA from other sturgeon tissue (blood from *A. stellatus*), as shown in Panel A, Lanes 6, 7 and 8. Lane 6 Chelex preparation blank, Lane 7 is a Chelex preparation from blood from *A. stellatus* used as a positive control, and Lane 8 is a negative PCR control. Lanes 6, 7 and 8 in Panel B are deliberately left blank.

Example II

Construction of Sturgeon Genetic Database

Table 1 lists the sturgeon species used in this study and where they were obtained. With three exceptions (*Acipenser brevirostrum, A. mikadoi*, and *A. oxyrinchus*), blood samples were taken, mixed with buffer (100 mM Tris, 100 MM EDTA, and 2% SDS; 0.5 ml of blood and 5 ml of buffer), and the blood cells lysed in this solution were kept in a freezer at −70° C. Most Russian specimens examined were the same individuals used for DNA content measurements by Birstein et al., *Genetica* 73: 3–12 (1993). DNA was isolated from alcohol-fixed samples of muscles of *Amia calva* and *Polypterus senegalus* provided by Paul Vrana (American Museum of Natural History, New York).

DNA was isolated from each sample using a standard phenol/chloroform preparation (DeSalle et al., 1993). Partial sequences of three ribosomal genes (two mitochondrial [12S and 16S] and one nuclear [18S]) and over 600 bases of the mitochondrial cytochrome b gene were examined for all of the species listed in Table 1. PCR products were prepared for DNA sequencing in several ways. In all cases the nuclear 18S rDNA fragments were GeneCleaned (BIO 101; Palumbi et al., *The Simple Fool's Guide* to PCR, Version 2, 1991) and directly sequenced. PCR products of the mitochondrial genes (12S, 16S, and cytochrome b) were either GeneCleaned and directly sequenced or cloned into the TA vector (INVITROGEN) and sequenced (in such cases, at least two clones for each taxon were used to establish the sequence). The following primers were used: in the 18S gene region, 18sai0.7 (5'-ATTAAAGTTGTTGCGGTTT-3') (SEQ ID NO: 1) and 18sai0.79 (5'-GGTGGCATTTTATTTTATTAGAGG-3') (SEQ ID NO:2) and 12SB (5'-CCGGTCTGAACTCAGATCACGT-3') (SEQ ID NO:3) [Kocher et al., *Proc. Natl. Acad. Sci. USA*, 86: 6196–6200 (1989); Hedges et al., *Herpetological Monographs*, 7: 64–76 (1993)], in the 16S gene region 16SA (5'-CGCCTGTTTACCAAAACAT-3') (SEQ ID NO:4) and 16SB (5'-CCGGTCTGAATCAGATCACGT-3') (SEQ ID NO:5) Palumbi et al. 1991), and in the cytochrome b region, H15149 (5'-AAACTGCAGCCCCTCAGAATGATATTTGTCCTCA-3') (SEQ ID NO:6) (ocher et al. 1989) and L14724 (5'-CGAAGCTTGATATGAAAAACCATCGTTG-3') (SEQ ID NO:7) [Meyer et al., *J. Mol. Evol.*, 31:359–364 (1990)]. All sequencing was performed using the Sequenase system (U.S. Biochemicals) and double-stranded templates. The results of this sequencing demonstrated that the variability in the mitochrondrial cyt b gene was most suitable for the design of diagnostic primers.

TABLE 1

| Species | Geographical Region/Collector | Number or blood (or tissue samples) |
|---|---|---|
| *Acipenser baerii* | Lena River (Siberia, Russia)/V. Birstein | 2 |
| *A. brevirostrum* | Connecticut River (MA, USA)/B. Kynard | (eggs) |
| *A. dabryanus* | Yangtze River (China)/ Q. Wei | 1 |
| *A. fulvescens* | Great Lakes (WI, USA)/ F. Binkowski | 1 |
| *A. gueldenstaedti* | Caspian Sea, Northern part, (Russia)/A. Vlasenko | 7 |
| *A. medirostris* | Columbia River (OR, USA)/J. North | 1 |
| *A. mikadoi* | Tumnin River (Russia Far East)/E. Artyukhin | 2 (fragments of muscles) |
| *A. naccarii* | Ferrara, Italy | 2 |
| *A. nudiventris* | Aral Sea (Uzbekistan, Central Asia)/V. Birstein | 2 |
| *A. oxyrinchus desotoi* | Pearl River (LA, USA)/ J. Waldman | 1 |
| *A. oxyrinchus oxyrinchus* | St. Lawrence (Quebec, Canada)/J. Waldman | 2 (fragments of muscles) |
| *A. persicus* | Caspian Sea, Southern part (Iran)/Pourkazemi | 1 |
| *A. ruthenus* | Volga River (Russia/ V. Birstein | 2 |
| *A. schrencki* | Amur River (Siberia, Russia)/V. Svirskii | 1 |
| *A. sinensis* | Yangtze River/Q. Wei | 1 |
| *A. stellatus* | Volga River/V. Birstein | 15 |
| *A. sturio* | Gironde River (France)/ P. Williot | 1 |
| *A. sturio* | Northern Sea, near the Dutch coast/L. Debus | 1 |
| *A. transmontanus* (White Sturgeon) | Columbia River (OR, USA)/J. North | 2 |
| *Huso dauricus* (Kaluga Sturgeon) | Amur River (Siberia, Russia)/V. Svirskii | 2 |
| *H. huso* | Caspian Sea, Northern part (Russia)/A. Vlasenko | 20 |
| *S. albus* | Yellowstone River (MT, USA)/H. Bollig | 1 |
| *Pseudoscaphirhynchus kaufmanni* (Large AmuDar shovelnose) | Amu-Darya River (Uzbekistan) | 2 |
| *Scaphirhynchus albus* (Pallid sturgeon) | Yellowstone River (MT, USA) | 2 |
| *Polyodon spathula* (American Paddlefish) | | 1 |
| *Psephurus gladius* | Yangtze River (China)/ Q.Wei | 1 |

Example III

Use of Primer Pairs on Authentic Samples

Figure 2:
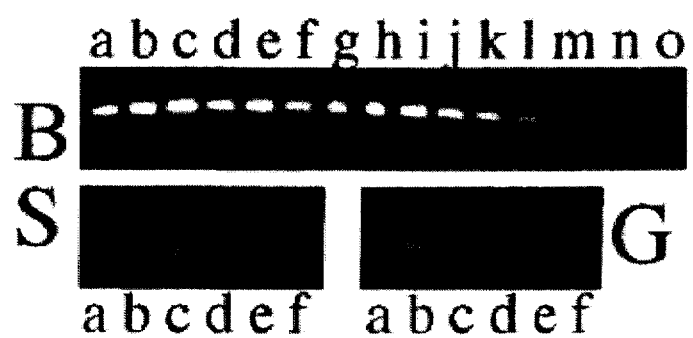
FIG. 2 shows the performance of three of the primer pairs used in the diagnosis of servuga (S), beluga (B), and osetra (G) caviar. The following primer pairs were used in the reactions: B3/B3an (Panel B); S2/S2an (Panel S); and, G3/S2an (Panel G). Lane a in all three panels is the PCR product generated from DNA made from caviar of the three species (from beluga caviar in Panel B, from servuga caviar in Panel S, and from osetra caviar in Panel G). Lanes m and n in Panel B were PCR products from *A. stellatus* and *A. gueldenstaedti*, respectively. Lanes d and e in Panel S were products from *H. huso* and *A. gueldenstaedti*, respectively. Lanes d and e in Panel G were products from *H. huso* and *A. stellatus*, respectively. Lanes n in Panel B, f in Panel S, and f in Panel G were PCR water negative controls.

DNA was isolated from single eggs after washing with 5.25% sodium hypochlorite by crushing the egg in homogenization buffer followed by Proteinase K (1 mg/ml final concentration) digestion for one hour at 65° C. Standard phenol/chloroform extraction (DeSalle et al., 1993) followed by two ethanol precipitations was performed to purify the DNA for PCR. PCR was performed using the primer pair (with one diagnostic primer and one anchor primer) indicated in Table 2 at 10M in 25 Ktl reactions. Gel electrophoresis results are shown in FIG. 2. DNA from 11 individuals of *H. huso* (Panel B, Lanes b through 1), two individuals of *A. stellatus* (Panel S, Lanes b and c) and two individuals of *A. gueldenstaedti* (Panel G, Lanes b and c)

was isolated from either tissue or blood and used as template for PCR reactions. Lane a in all three Panels is the PCR product generated from DNA made from caviar of the three species (from beluga caviar in Panel B, from servuga caviar in Panel S, and from osetra caviar in Panel G). Lanes m and n in Panel B were PCR products from *A. stellatus* and *A. gueldenstaedti*, respectively. Lanes d and e in Panel S were products from *H. huso* and *A. gueldenstaedti*, respectively. Lanes d and e in Panel G were products from *H. huso* and *A. stellatus*, respectively. Lanes n in Panel B, f in Panel S, and f in Panel G were PCR water negative controls. The following primer pairs (see Table 2) were used in the reactions: B3/B3an (Panel B); S2/S2an (Panel S); and, G3/S2an (Panel G). The PCR conditions were 94° C. for 1 minute, 55° C. for 1 minute, and 72° C. for 1 minute for 25 cycles. PCR products were assayed on 1.5% agarose in 1X TBE at 140 V for 20 to 30 minutes in a BioRad miniature submersible electrophoresis rig. DNA was visualized under UV light after staining the gel in ethidium bromide. For all figures the gels were photographed using Polaroid film and scanned into Adobe Photoshop and manipulated using this program.

The G primers were difficult to design as entirely specific for *A. gueldenstaedti* (osetra) because of the close relatedness of this species to the other members of the clade of Eurasian sturgeons (*A. baerii, A. persicus, A. naccarii, A. nudiventris,* and *A. dabryanus*). Hence, two primers were designed that in combination could diagnose the osetra caviar. The G3 primer pair is specific for *A. gueldenstaedti, A. persicus, A. naccarii, A. baerii, A. nudiventris, A. dabryanus,* and *A. brevirostrum*. The G4 primer pair is specific for *A. gueldenstaedti, Scaphirhynchus albus, Polyodon spathula,* and *Psephurus gladius*.

TABLE 2

| Primer Pair | Species Specificity | SEQ ID NO | Primer Sequence |
|---|---|---|---|
| B2 | Huso huso | 8 | gcaaacggggcctcctc |
| B2a | B2 anchor | 9 | cagaatgatatttggcctca |
| B3 | Huso huso | 10 | cactacacagctgacatc |
| B2an | B3 anchor | 11 | cagaatgatatttggcctca |
| S1 | A. stellatus | 12 | ctttctgccttcccgtat |
| S1an | S1 anchor | 13 | gaagaaagtggaaggcg |
| S2 | A. stellatus | 14 | ggagtcctaggccctcctg |
| S2an | S2 anchor | 15 | cctccaattcatgtgagtact |

TABLE 2-continued

| Primer Pair | Species Specificity | SEQ ID NO | Primer Sequence |
|---|---|---|---|
| G3 | A. gueldenstaedti | 16 | aataaactaggtggagtt |
| S2an | G3 anchor | 17 | cctccaattcatgtgagtact |
| G4 | A. gueldenstaedti | 18 | atgaatctgaggcggcttc |
| S1an | G4 anchor | 19 | gaagaaagtggaaggcg |

Example IV

Use of Primers for Identification of Less Common Species

DNA is isolated from single eggs after washing with 5.25% sodium hypochlorite by crushing the egg in homogenization buffer followed by Proteinase K (1 mg/ml final concentration) digestion for one hour at 65° C. Standard phenol/chloroform extraction (DeSalle et al., 1993) followed by two ethanol precipitations is performed to purify the DNA for PCR. PCR is performed as described in the previous examples using a cocktail made up of two or more primer pairs, where one member of the pair is a diagnostic primer given in Table 3 and the other member of the pair is a matched anchor primer. PCR products are assayed on 1.5% agarose in 1X TBE at 140 V for 20 to 30 minutes in a BioRad miniature submersible electrophoresis rig. DNA is visualized under UV light after staining the gel in ethidium bromide. If no PCR products are visible, the process is repeated with other cocktails of primer pairs until the species origin of the sample is identified.

Table 3 lists sequences in the 5' to 3' direction for primers specific to the sturgeon species given. The diagnostic 3'-most base is designated by a space between it and the rest of the primer. Table 4 lists sequences in the 3' to 5' direction for additional diagnostic primers for the sturgeon species given. The diagnostic 3'-most base is designated by a space between it and the rest of the primer. The primer code used for these "reverse" primers includes a lower case "r" to indicate that these sequences run in the 3' to 5' direction. In both Table 3 and 4, the sturgeon genus is *Acipenser* unless otherwise specified.

TABLE 3

| Primer | Species Specificity | SEQ. ID NO | Primer Sequence |
|---|---|---|---|
| N16 | nudiventris | 20 | CGCAACCGTGATCACCAACCTCCTTT A |
| S17 | stellatus | 21 | CGCAACCGTGATCACCAACCTCCTTTC T |
| M20 | medirostris | 22 | CGCAACCGTGATCACTAACCTCCTTTCCGC T |
| P35 | Polyodon | 23 | CCTCCTTTCCGCCTTCCCCTACATCGG G |
| Ps35 | Psepherus | 24 | CCTCCTTTCCGCCTTCCCCTAGATCGG A |
| O41 | oxyrhincus | 25 | TCTCCGCCTTCCCATACATCGGCGACAC G |
| P41 | Polyodon | 26 | TCTCCGCCTTCCCCTACATCGGGGACAC C |
| O46 | oxyrhincus | 27 | TTCCCATACATCGGCGACACGCTAG G |
| O50 | oxyrhincus | 28 | TTCCCATACATCGGCGACACGCTAGGTCA G |
| B42 | brevirostrum | 29 | TCTCCGCCTTCCCGTACATCGGCGACACA T |
| P62 | Polyodon | 30 | GACACCCTAGTACAATGAATCTGAGG T |
| Nc62 | nacarri | 31 | GACACACTAGTACAATGAATCTGAGG T |
| T72 | transmontanus | 32 | AGTTCAATGAATCTGAGGCGGCTTTTCA C |
| P89 | Polyodon | 33 | TGGGTTCTCAGTAGACAACGCCACCCT A |
| Ps89 | Psepherus | 34 | TGGGTTCTCAGTAGACAACGCCACCCT G |
| Si101 | schrenki | 35 | TAGACAATGCCACCCTTACCCGATTCTT T |
| P107 | Polyodon | 36 | ACCCTAACCCGATTCTTCGCCT A |

TABLE 3-continued

| Primer | Species Specificity | SEQ. ID NO | Primer Sequence |
|---|---|---|---|
| Hd115 | H. dauricus | 37 | CCCGATTTTTCGCCTTCCACTTT G |
| St47 | sturio | 38 | ATACATCGGCGACACACTAGT G |
| B29 | baerii | 39 | TCACTAACCTCCTCTCCGCCTTTCCGTA T |
| B91 | baerii | 40 | CTTTTCAGTAGACAACGCCACCCTTA G |
| G68 | gueldenstadti | 41 | TACAATGAATCTGAGGCGGCTT C |
| G114 | gueldenstadti | 42 | CCGATTCTTCGCCTTCCACTT C |
| T133 | transmontanus | 43 | CACCCCCACACATCAAACCCGAATG G |
| Ps160 | Psepherus | 44 | GTGATACTTCCTCTTTGCCTACGCCATCCT T |
| R171 | ruthenus | 45 | TTTGCCTACGCCATTCTCCGATCCATCC T |
| S190 | stellatus | 46 | CGATCTATCCCAAACAAACTAGGCGGAGT C |
| P202 | Polyodon | 47 | ACAAACTAGGTGGGGTACTGGCCCTACT T |
| S202 | stellatus | 48 | ACAAACTAGGCGGAGTCCTAGCCCTCCT G |
| P205 | Psepherus | 49 | GGAGTACTAGCCCTACTATT A |
| T115 | transmontanus | 50 | GAGTACTAGCCCTTCTATTTTCCATCCT G |
| T221 | transmontanus | 51 | GCCCTTCTATTTTCCATCCTGGTCCTA G |
| T222 | transmontanus | 52 | GCCCTTCTATTTTCCATCCTGGTCCTAG C |
| S250 | stellatus | 53 | TAGTGCCAATGCTTCACACCTCTAA G |
| O274 | oxyrhincus | 54 | CAAACAACGAGGAAATACATTTCGGCC T |
| O284 | oxyrhincus | 55 | GAGGAAATACATTTCGGCCTCTCTCCCAA G |
| Si281 | schrenki | 56 | CGCCATTCTCGGAAACACATTCCGACCCCTCCGG T |
| Si279 | schrenki | 57 | CGCCATTCTCGGAAACACATTCCGACCCCTCC G |
| T286 | transmontanus | 58 | ATTCTCGGAAACACATTCCGACCCCTTTCTCAAAT G |
| F318 | fulvus | 59 | ATTCTGGACCCTAGTGGCGACATACTAGT G |
| P306 | Polyodon | 60 | CTCAAATCCTATTCTGGACCTAGTAGG T |
| M395 | mikaido | 61 | ATTATTTCTCGCAATACACTA T |
| Hd405 | H. dauricus | 62 | GCAATACACTACACAGCTG G |
| Hh408 | H. huso | 63 | GCAATACACTACACAGCTGACAT C |
| Hh457 | H. huso | 64 | CACATCTGCCGAGACGTAAATTA T |
| Hd459 | H. dauricus | 65 | GCCCACATCTGCCGGGATGTAAATTACGG C |
| Hd465 | H. dauricus | 66 | GCCCACATCTGCCGGGATGTAAATTACGGCTGA T |
| Br461 | brevirostrum | 67 | GCCCACATCTGCCGAGACGTAAATTACGGAT A |
| M466 | mikaido | 68 | AGATGTAAATTACGGATGGCT T |
| Sc475 | Scaphyrhincus | 69 | ACGGGTGACTAATCCGAAAC G |
| Sc489 | Scaphyrhincus | 70 | CGAAACGTCCACGCAAATGG C |
| Si489 | schrenki | 71 | CGAGATGTGAATTACGGATG C |
| Hd471 | H. dauricus | 72 | GGATGTAAATTACGGCTGATTAATCCG C |
| P441 | Polyodon | 73 | CCTCCGTCGCCCACATCTG T |
| D492 | dabyrynus | 74 | AAATATTCATGCAAACGGGGC T |
| Hh498 | H. huso | 75 | TCCGAAATATTCATGCAACGGGGCCTCCT C |
| Hh536 | H. huso | 76 | ATCTTCACGTAGCACGAGGT T |
| Hh540 | H. huso | 77 | ATCTTCACGTAGCACGAGGTTTGTA T |
| N549 | naccari | 78 | CGGGGTATATACTATGGTTC G |
| N573 | naccari | 79 | TCCAAAAAGAAACCTGAAA T |
| Hh556 | H. huso | 80 | CGTAGCACGAGGTTTGTATTACGGTTCATACCT T |
| Hd552 | H. dauricus | 81 | GCATGTACTACGCTTCCTA T |
| Pc565 | persicus | 82 | GTTCATACCTCCAAAAAGA G |

TABLE 4

| Primer | Species Specificity | SEQ ID NO | Primer Sequence |
|---|---|---|---|
| rN16 | nudiventris | 83 | T GCGGAAGGGCATGTAGCCGCTGTG |
| rS17 | stellatus | 84 | A CGGAAGGGCATATAGCCGCTGTG |
| rM20 | medirostris | 85 | A AAGGGCATGTAGCCGCTGTG |
| rP35 | Polyodon | 86 | C CTGTGGGATCATGTTACTTAGACTC |
| rPs35 | Psepherus | 87 | T CTGTGTGATCATGTTACTTAGACTC |
| rO41 | oxyrhincus | 88 | C GATCCAGTCACTTAGACTC |
| rP41 | Polyodon | 89 | G GATCATGTTACTTAGACTC |
| rO46 | oxyrhincus | 90 | C AGTCACTTAGACTCCGCCGAAAAGTCACCTGTTG |
| rO50 | oxyrhincus | 91 | C ACTTAGACTCCGCCGAAAAGTCACCTGTTG |
| rB42 | brevirostrum | 92 | A ATCACGTTACTTAGACTCCGCCGAAAAG |
| rP62 | Polyodon | 93 | A CCCAAGAGTCATCTGTTGCGGTGGGATT |
| rNc62 | naccari | 94 | A CCGAAAAGTCATCTGTTGCGGTGGG |
| rT72 | transmontanus | 95 | G ATCTGTTACGGTGGGAATGGG |
| rP89 | Polyodon | 96 | T TGGGCTAAGAAGCGGATGGTG |
| rPs89 | Psepherus | 97 | C TGGGCTAAGAAGCGGAAGGTG |
| rSi101 | schrenki | 98 | A CGGAAGGTGAAAGAGGATGG |
| rP107 | Polyodon | 99 | T GGTGAAAGAAGATGGCATTC |
| rHd115 | H. dauricus | 100 | C AAGATGGTAAGCATTAGCGGCCTCGATCG |
| rSt47 | sturio | 101 | C GTTACTTAGACTCCGCCGA |
| rB29 | baeriI | 102 | A TAGCCGCTGTGTGATCATG |
| rB91 | baerii | 103 | C GGCTAAAAAGCGGAAGGTGA |

TABLE 4-continued

| Primer | Species Specificity | SEQ ID NO | Primer Sequence |
|---|---|---|---|
| rG68 | gueldenstadti | 104 | G AGTCATCTGTTGCGGTGGGA |
| rG114 | gueldenstadti | 105 | G GAGGACGGTAAACATTAGCGGCCTCGA |
| rT133 | transmontanus | 106 | C ATGAAAGAGAAACGGATGCGGTAAGAG |
| rPs160 | Psepherus | 107 | A GCTAGGTAGGGTTTGTTTGA |
| rR171 | ruthenus | 108 | A TTTATTTGATCCACCTCAT |
| rS190 | stellatus | 109 | G GATCGGGAGGACAAGAGATA |
| rP202 | Polyodon | 110 | A AAGAGGTAGGATCATGATTA |
| rS202 | stellatus | 111 | C AAGAGATAGGATCATGATTA |
| rP205 | Psepherus | 112 | T AGGTAGGATCATGATTATGA |
| rT115 | transmontanus | 113 | C CAGGATCGTAACCATGGTT |
| rT221 | transmontanus | 114 | C GTAACCATGGTTATGAGGT |
| rT222 | transmontanus | 115 | G TAACCATGGTTATGAGGT |
| rS250 | stellatus | 116 | G TTGCTCCTTTGTGCAAAGC |
| rO274 | oxyrhincus | 117 | A GAGAGGGTTCAGGATAAAA |
| rO284 | oxyrhincus | 118 | C AGGATAAAACTCGGGATCACC |
| rSi281 | schrenki | 119 | A TTTAGGATAAGACCCGGGA |
| rSi279 | schrenki | 120 | C CATTTAGGATAAGACCCGGGA |
| rT286 | transmontanus | 121 | C GATAAGACCCGGGATCACCG |
| rF318 | fulvus | 122 | C GAGTGTACTTAGCCTCCGGTTGGTCAGCTTGTGGG |
| rP306 | Polyodon | 123 | A CTATACAATCATGAGTGTA |
| rM395 | mikaido | 124 | A TGTCGACTGTAAAGTTGTC |
| rHd405 | H. dauricus | 125 | C GTAAAGTTGTCGGAAGAGG |
| rHh408 | H. huso | 126 | G AGTTGTCGGAAGAGGAGGC |
| rHh457 | H. huso | 127 | A CCTACTGATTAGGCTTTATA |
| rHd459 | H. dauricus | 128 | G ACTAATTAGGCGTTATAAGTACG |
| rHd465 | H. dauricus | 129 | A ATTAGGCGTTATAAGTACG |
| rBr461 | brevirostrum | 130 | T TGATTAGGCTTTATAAGTAC |
| rM466 | mikaido | 131 | A TAGGCTTTATAAGTACGTTT |
| rSc475 | Scaphyrhincus | 132 | C AGGTGCGTTTACCGCGGAGGA |
| rSc489 | Scaphyrhincus | 133 | G CGGAGGAAGAAGAAATAGAC |
| rSi489 | schrenki | 134 | G GATTAGGCTTTGTAAGTACG |
| rHd471 | H. dauricus | 135 | G ACTAATTAGGCGTTATAAGTA |
| rP441 | Polyodon | 136 | A GCTCTACAATTGATGCCTAC |
| rD492 | dabyrynus | 137 | A AGAAAGAAGAAATAGACGA |
| rHh498 | H. huso | 138 | A ACATAATGCCAAGTATGGAAGTTTT |
| rHh536 | H. huso | 139 | A ATGCCAAGTATGGAAGTTTT |
| rHh540 | H. huso | 140 | G GAAGAAGTAGACGAACATAGAAGTGC |
| rN549 | naccari | 141 | C ATGGAGGTTTTTCTTTGGAC |
| rN573 | naccari | 142 | A TAACCTCATAAGGAGAACGAAGAGTGG |
| rHh556 | H. huso | 143 | A GTTTTTCTTTGGACTTTGTA |
| rHd552 | H. dauricus | 144 | A GAGGTTTTTCTTTGGACTTT |
| rPc565 | persicus | 145 | C TGGACTTTGTAGCCTCATA |

Example V

Determination of Species Origin for Commercial Caviar Samples

Figure 3:
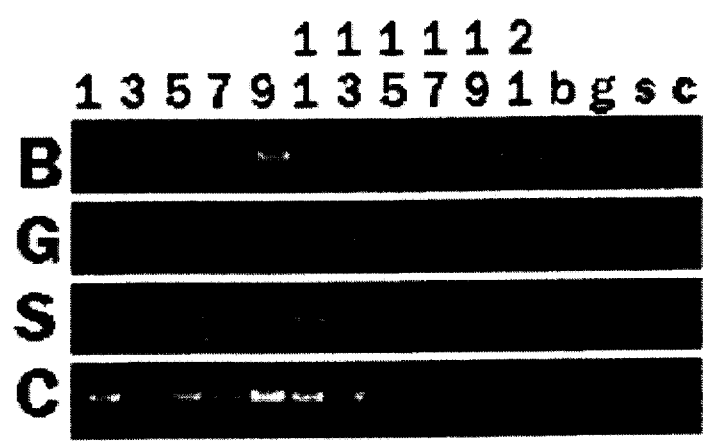
FIG. 3 shows the results of a PCR assay on DNA isolated from single eggs from lots of commercially available caviar. DNA from five to ten individual eggs was isolated for each commercial lot. Only a single representative is shown from each odd-numbered lot as all eggs from a given lot gave the same results. Results for odd-numbered lots 1 through 21 are shown. PCR products using beluga (Panel B; B3/B3an), servuga (Panel S; S2/S2an) and osetra (Panel G; G3/S2an) primer pairs are shown in this figure. A fourth primer pair was used as a positive control and was designed to amplify all sturgeon samples (C).

Initially, DNA from five to ten individual eggs was isolated for each commercial lot. Results are illustrated in FIG. 3, where only a single representative from each odd numbered lot is shown as all eggs from a lot gave the same results. Lot numbers were arbitrarily assigned to the commercially available lots. Results for even numbered lots are not shown, but are reported in Table 5. The species designations of the lots as given by the commercial suppliers are listed in Table 5. PCR products using beluga (Panel B; B3/B3an), servuga (Panel S; S2/S2an) and osetra (Panel G; G3/S2an) primer pairs (Table 2) are shown in FIG. 3. A fourth primer pair was used as a positive control and was designed to amplify all sturgeon samples (C).

None of the lots gave positive reactions for more than one of the diagnostic primer pairs (B, G or S). These results are verified using other primer pairs (Table 2) and, in some cases (see below), the double stranded fragment produced by the positive control (Panel C) for these four lots was GeneCleaned (BIO 101) and sequenced using an ABI Model 373 automated sequencer. Several positions in this fragment are diagnostic for other species and these nucleotide positions were used to type these four lots (Table 5). Sample 3 although showing a positive reaction in Panel G, did not show a positive reaction for the G4/S 1 an primer pair. The control PCR product was therefore sequenced and used to diagnose this lot of caviar. Samples 4 and 12 were the only samples that were negative for all three primer pairs, but positive for the control primers. Control PCR of these three lots of caviar as well as lots Nos. 1, 9, 13, and 16 were GeneCleaned and sequenced to determine the source species used for making these caviars (see Table 5). As is evident from Table 5, the source species for five of the twenty-five commercial samples of caviar tested did not correspond to the species given on the product label.

TABLE 5

| Caviar Lot | Designation by Supplier (Trade Name) | Diagnosis |
|---|---|---|
| 1. | American sturgeon | Osetra |
| 2. | Caspian beluga | Beluga |
| 3. | Caspian osetra | Ship sturgeon |
| 4. | Eastern beluga | Amur River sturgeon |
| 5. | Caspian servuga | Servuga |
| 6. | Fresh beluga malossol | Servuga |
| 7. | Fresh ossetra malossol | Osetra |
| 8. | Fresh servuga malossol | Servuga |
| 9. | Caviar Russ (beluga) | Beluga |

TABLE 5-continued

| Caviar Lot | Designation by Supplier (Trade Name) | Diagnosis |
|---|---|---|
| 10. | Russian caviar (osetra) | Osetra |
| 11. | Servuga malossol | Servuga |
| 12. | Beluga malossol | Siberian sturgeon |
| 13. | Osetra malossol | Osetra |
| 14. | Servuga malossol | Servuga |
| 15. | Beluga malossol | Beluga |
| 16. | Osetra malossol | Osetra |
| 17. | Servuga malossol | Servuga |
| 18. | Sturgeon caviar | Osetra |
| 19. | Russian caviar | Servuga |
| 20. | Servuga malossol | Servuga |
| 21. | Beluga prime Beluga | Beluga |
| 22. | Oscetra malassol | Osetra |
| 23. | Beluga malossol | Beluga |
| 24. | Ossetra malassol | Osetra |
| 25. | Servuga malossol | Servuga |

Unless defined otherwise, all technical and scientific terms used herein have the same meaning as commonly understood by one of ordinary skill in the art to which this invention belongs.

It is understood that the examples and embodiments described herein are for illustrative purposes only and that various modifications or changes in light thereof will be suggested to persons skilled in the art and are to be included within the scope of the application and the appended claims.

We claim:

1. A method of determining a species origin of caviar, said method comprising the steps of:

a) obtaining a sample of caviar;

b) cleaning the surface of the caviar with an agent capable of removing salt and other debris from the surface of the caviar without damaging the caviar;

c) extracting template DNA from said sample;

d) amplifying extracted template DNA by using at least one primer pair consisting of a species-specific diagnostic primer which binds to a nucleotide position diagnostic of a species of said caviar and an anchor primer matched with the diagnostic primer such that the anchor primer binds to a nucleotide position no more than about 250 nucleotides away from said nucleotide position, wherein said diagnostic primer hybridizes one or more DNA fragments having a sequence complementary any of the sequences shown in SEQ. ID NO:8, SEQ. ID NO:10, SEQ. ID NO:12, SEQ. ID NO:14, SEQ. ID NO:16, SEQ. ID NO:18, or SEQ. ID NO:20 through SEQ. ID NO:145; and e) analyzing the products for the presence or absence of amplified DNA.

2. A method according to claim 1, wherein said sample is a single egg of commercially processed caviar.

3. A method according to claim 1, wherein said agent for removing salt and other debris comprises a solution selected from the group consisting of saline solution, dilute acids, dilute bases, mild detergent solutions, DNA extraction buffer and sodium hypochlorite solution, wherein the concentration of said solution does not lyse the caviar eggs.

4. A method according to claim 1, wherein said extracting is by phenol/chloroform extraction.

5. A method according to claim 1, wherein said analyzing comprises the steps of assaying said products by gel electrophoresis and detecting said products.

6. A method according to claim 5, wherein said detecting is by staining with ethidium bromide, propidium iodide or silver.

7. A method for identifying a species from which fish tissue originates, said method comprising the steps of:

a) removing salt and debris from the outer surface of a fish egg from the same fish from which said fish tissue originated;

b) isolating template DNA from said egg;

c) amplifying said template DNA by use of the polymerase chain reaction (PCR) using a cocktail of primers containing at least a pair of primers in which one primer is a diagnostic primer specific for a sturgeon species of interest and which binds to a nucleotide position diagnostic of said sturgeon species and the other primer is an anchor primer matched with said diagnostic primer such that the anchor primer binds to a nucleotide position no more than about 250 nucleotides away from said nucleotide position, wherein said diagnostic primer hybridizes one or more DNA fragments having a sequence complementary any of the sequences shown in SEQ. ID NO:8, SEQ. ID NO:10, SEQ. ID NO:12. SEQ. ID NO:14, SEQ. ID NO:16, SEQ. ID NO:18, or SEQ. ID NO:20 through SEQ. ID NO:145;

d) assaying the PCR products; and e) detecting the results.

8. The method of claim 7 wherein the steps of the method are repeated using primers specific for different species until a positive identification is made.

9. The method according to claim 7 wherein said removing is washing with a cleaning solution.

10. The method according to claim 7 wherein said isolating is by phenol/chloroform extraction.

11. The method according to claim 7 wherein said assaying is by gel electrophoresis and said detecting is by staining with ethidium bromide, propidium iodide or silver.

12. A primer which hybridizes one or more DNA fragments having a sequence complementary to one or more of the sequences set forth in SEQ. ID NO:8, SEQ. ID NO:10, SEQ. ID NO:12, SEQ. ID NO:14, SEQ. ID NO:16, SEQ. ID NO:18, and SEQ. ID NO:20 through SEQ. ID NO:145.

13. A primer cocktail comprising a plurality of primer pairs wherein said primer pairs each consist of a diagnostic primer specific for a sturgeon species of interest and which binds to a nucleotide position diagnostic of said sturgeon species and an anchor primer matched with said diagnostic primer such that the anchor primer binds to a nucleotide position no more than about 250 nucleotides away from said nucleotide position, wherein said diagnostic primer hybridizes one or more DNA fragments having a sequence complementary any of the sequences set forth in SEQ. ID NO:8, SEQ. ID NO:10, SEQ. ID NO:12, SEQ. ID NO:14, SEQ. ID NO:16, SEQ. ID NO:18, or SEQ. ID NO:20 through SEQ. ID NO:145.

* * * * *